US008620417B2

(12) United States Patent
Turgeman et al.

(10) Patent No.: US 8,620,417 B2
(45) Date of Patent: Dec. 31, 2013

(54) GRAPHIC USER INTERFACE FOR PHYSICAL PARAMETER MAPPING (75) Inventors: Aharon Turgeman, Zichron Ya'acov (IL); Natan Katz, Kiryat Bialik (IL); Gal Hayam, Tivon (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 0 days.

(21) Appl. No.: 13/240,162

(22) Filed: Sep. 22, 2011

(65) Prior Publication Data
US 2013/0079650 A1    Mar. 28, 2013

(51) Int. Cl.
*A61B 5/044*   (2006.01)
(52) U.S. Cl.
USPC ............................ 600/523; 600/437; 600/410
(58) Field of Classification Search
USPC ................... 600/459, 450, 523, 410, 437
See application file for complete search history.

(56) References Cited

U.S. PATENT DOCUMENTS

| 2005/0096540 A1* | 5/2005 | Ooshima ............... 600/437 |
| 2006/0084972 A1 | 4/2006 | Beatty et al. |
| 2009/0069704 A1* | 3/2009 | MacAdam et al. ...... 600/523 |

FOREIGN PATENT DOCUMENTS

EP          1 929 956 A2    6/2008
WO   WO 2008/091827 A2    7/2008

OTHER PUBLICATIONS

Extended European Search Report dated Dec. 21, 2012 from related European Application No. 12185374.1.

* cited by examiner

*Primary Examiner* — Christopher D Koharski
*Assistant Examiner* — Natasha Patel
(74) *Attorney, Agent, or Firm* — Louis J. Capezzuto (57) ABSTRACT

A method, including measuring values of a physical parameter at multiple locations in an organ of a subject, and analyzing the measured values to identify a range of the values, including at least one sub-range containing one or more values that were not measured. The method further includes receiving a selection from a user of a value in the sub-range, and, responsive to the selection, displaying a candidate location for further measurement.

18 Claims, 7 Drawing Sheets

GRAPHIC USER INTERFACE FOR PHYSICAL PARAMETER MAPPING

FIELD OF THE INVENTION

The present invention relates generally to measuring of a physical parameter in an organ of a subject, and specifically to a graphic user interface for facilitating the measurement.

BACKGROUND OF THE INVENTION

In medical procedures, such as mapping the electrical activity of the heart, it is typically preferable to perform the procedure as quickly as possible. However, the requirement to complete the procedure in as short a time as possible may lead to inefficiencies in the collection of results. A system to reduce the inefficiencies is thus beneficial.

SUMMARY OF THE INVENTION

An embodiment of the present invention provides a method, including:

measuring values of a physical parameter at multiple locations in an organ of a subject;

analyzing the measured values to identify a range of the values, including at least one sub-range containing one or more values that were not measured;

receiving a selection from a user of a value in the sub-range; and responsive to the selection, displaying a candidate location for further measurement.

Typically, the organ includes a heart. The physical parameter may be evaluated in response to one of a force exerted by the heart and a temperature of the heart. Alternatively, the physical parameter may be evaluated in response to electrical activity of the heart.

In a disclosed embodiment the physical parameter includes respective local activation times (LATs) of the multiple locations in the heart. Typically, measuring the values includes recording respective time-varying electrical potentials at the multiple locations, and analyzing the measured values includes determining the respective LATs in response to applying a predefined condition to the recorded time-varying electrical potentials.

In an alternative embodiment displaying the candidate location includes displaying an image of the heart to the user, and indicating on the image the candidate location.

In a further alternative embodiment analyzing the measured values includes displaying to the user a first visual representation of values that were measured, and a second visual representation, different from the first visual representation, of the at least one sub-range. Typically, receiving the selection from the user includes the user operating a pointing device to select a region in the second visual representation. The first and second visual representations may be formed as a number line.

There is further provided, according to an embodiment of the present invention, apparatus, including:

a probe, which is configured to provide signals used to measure values of a physical parameter at multiple locations in an organ of a subject; and a processor which is configured to:

analyze the measured values to identify a range of the values, including at least one sub-range containing one or more values that were not measured;

receive a selection from a user of a value in the sub-range; and responsive to the selection, display a candidate location for further measurement.

The present disclosure will be more fully understood from the following detailed description of the embodiments thereof, taken together with the drawings, in which:

DETAILED DESCRIPTION OF EMBODIMENTS

Overview

An embodiment of the present invention provides a method for improving the measuring of values of a physical parameter at multiple locations in an organ of a human subject. Typically, the physical parameter may be any parameter that may be measured at each of the multiple locations of the organ using an electrical sensor such as an electrode, a mechanical sensor such as a force sensor, or a temperature sensor. Examples of parameters that may be measured at each location include, but are not limited to, impedance, local activation time (LAT), contractility, temperature, and exerted force. The organ may be any organ in the subject, but for simplicity, except where otherwise indicated, in the following description the organ is assumed to be the heart of the subject.

A user of the method typically records at the multiple locations a set of measurements of the heart to be used for evaluating the parameter. A processor analyzes each measurement to evaluate the parameter for the location at which the measurement was recorded. The processor may be able to derive a value of the parameter from the measurement; alternatively, a measurement may not generate a value of the parameter.

After all the measurements have been analyzed, the results may be displayed to the user on a number line of the parameter. The number line typically displays two types of numbers, a first type wherein the parameter has been evaluated, and a second type wherein the parameter has not been evaluated. The two types are displayed in a visually differentiated manner. For example, the first type, wherein the parameter has been evaluated, may be shown in a first color, and the second type, wherein the parameter has not been evaluated, may be shown in a second color.

The user may position a cursor on a region of the second color (i.e. on a number for which there is no evaluated parameter). From this position, the processor indicates a location, typically on a three-dimensional image of the heart, which the processor considers is a candidate location for re-measurement of the parameter. The processor selects the candidate location from the locations at which recordings were made in the set of measurements, but where a value of the parameter was not able to be evaluated.

The user may re-measure at the indicated location to generate signals for the processor, which analyzes the new signals to determine the parameter for the indicated location. Typically the number line is updated to reflect the now known value of the parameter, and the user may repeat the process described above until the number line shows only the first color, showing that the parameter has been measured for all sampled locations of the heart.

System Description

Figure 1:
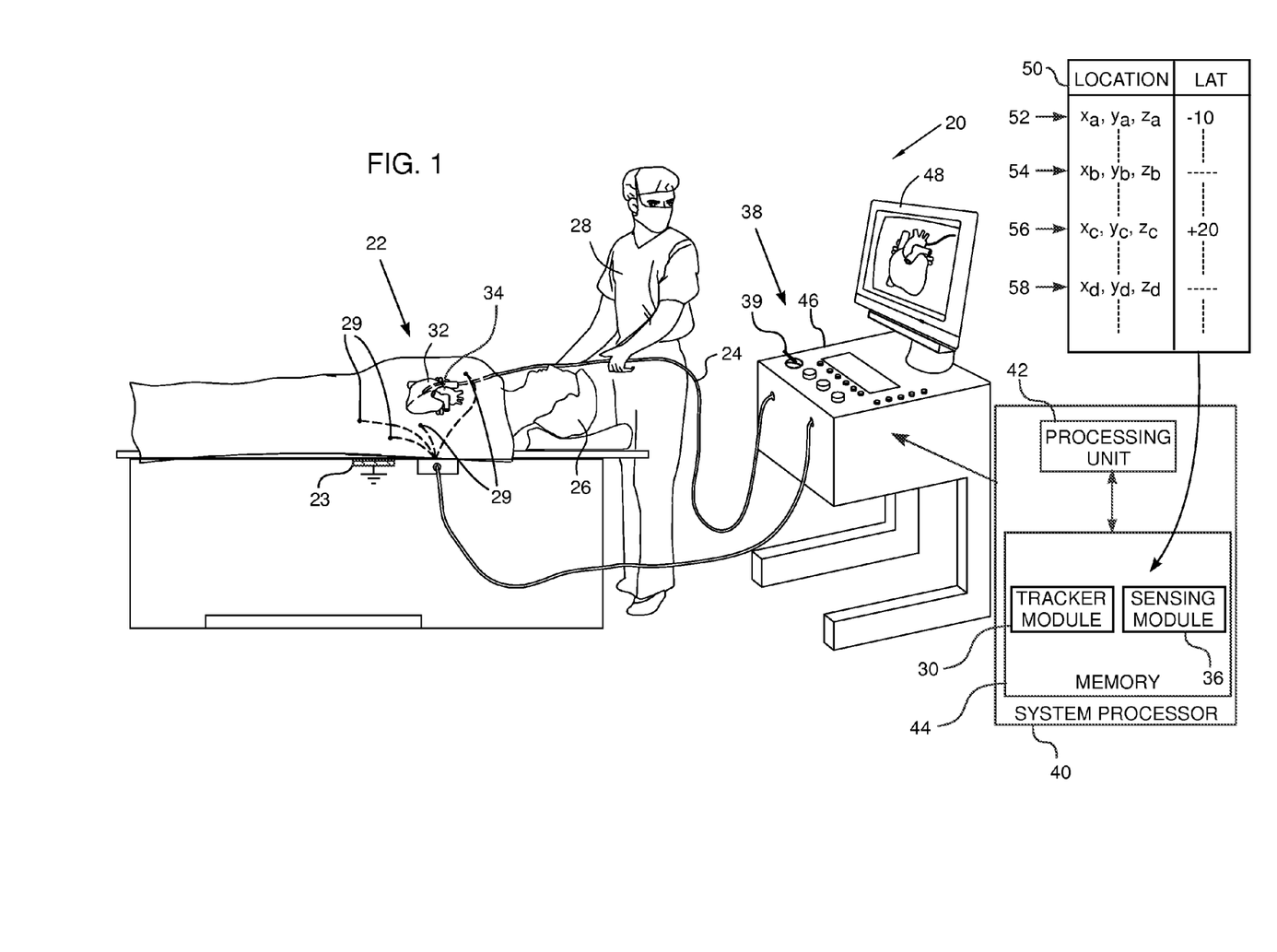
FIG. 1 is a schematic illustration of a physiological mapping system, according to an embodiment of the present invention.

Reference is now made to FIG. 1, which is a schematic illustration of a physiological mapping system 20, according to an embodiment of the present invention. System 20 uses a sensor 22 on a distal end 32 of a probe 24 in order to map a characteristic parameter of an organ of a human subject 26. In one embodiment sensor 22 comprises an electrode. Alternatively or additionally, sensor 22 comprises another type of sensor configured to sense a physical measurement, such as a force sensor or a temperature sensor.

In the description herein the organ being mapped is assumed, by way of example unless otherwise indicated, to be a heart 34 of the subject. Typically, probe 24 comprises a catheter which is inserted into the body of subject 26 during a mapping procedure performed by a user 28 of system 20. In the description herein user 28 is assumed, by way of example, to be a medical professional. During the procedure subject 26 is assumed to be attached to a grounding electrode 23. In addition, electrodes 29 are assumed to be attached to the skin of subject 26, in the region of heart 34.

System 20 may be controlled by a system processor 40, comprising a processing unit 42 communicating with a memory 44. Processor 40 is typically mounted in a console 46, which comprises operating controls 38, typically including a pointing device 39 such as a mouse or trackball, that professional 28 uses to interact with the processor. The processor uses software, including a probe tracker module 30 and a sensing module 36, stored in memory 44, to operate system 20. The sensing module is configured according to sensor 22. For example, if sensor 22 comprises a force sensor, module 36 generates a value of the force on the sensor. If sensor 22 comprises an electrode, module 36 generates a value of an electrical parameter, such as a local activation time or an impedance, from signals sensed by the electrode.

Results of the operations performed by processor 40 are presented to the professional on a display 48, which typically presents a graphic user interface to the operator, and/or an image of heart 34 while it is being mapped. The software may be downloaded to processor 40 in electronic form, over a network, for example, or it may, alternatively or additionally, be provided and/or stored on non-transitory tangible media, such as magnetic, optical, or electronic memory.

Probe tracker module 30 tracks sections of probe 24 while the probe is within subject 26. The tracker module typically tracks both the location and orientation of distal end 32 of probe 24, within the heart of subject 26. In some embodiments module 30 tracks other sections of the probe. The tracker module may use any method for tracking probes known in the art. For example, module 30 may operate magnetic field transmitters in the vicinity of the subject, so that magnetic fields from the transmitters interact with tracking coils located in sections of the probe being tracked. The coils interacting with the magnetic fields generate signals which are transmitted to the module, and the module analyzes the signals to determine a location and orientation of the coils. (For simplicity such coils and transmitters are not shown in FIG. 1.) The Carto® system produced by Biosense Webster, of Diamond Bar, Calif., uses such a tracking method. Alternatively or additionally, tracker module 30 may track probe 24 by measuring impedances between electrode 23, electrodes 29 and sensor 22 (if the sensor comprises an electrode), as well as the impedances to other electrodes which may be located on the probe. The Carto3® system produced by Biosense Webster uses both magnetic field transmitters and impedance measurements for tracking.

During operation of system 20, processor 40 stores in memory 44 a set 50 of pairs of locations as determined by the tracker module, and results of an analysis performed by the processor. For example, sensor 22 may comprise an electrode, and sensing module 36 and processor 40 may be configured to generate values of the local activation time (LAT) at sampled locations of the heart. In this case set 50 comprises pairs of locations and LATs, as is illustrated in FIG. 1. Four pairs 52, 54, 56, and 58 are shown in FIG. 1. The set, shown by way of example as a table in FIG. 1, is explained in more detail below.

Figure 2:
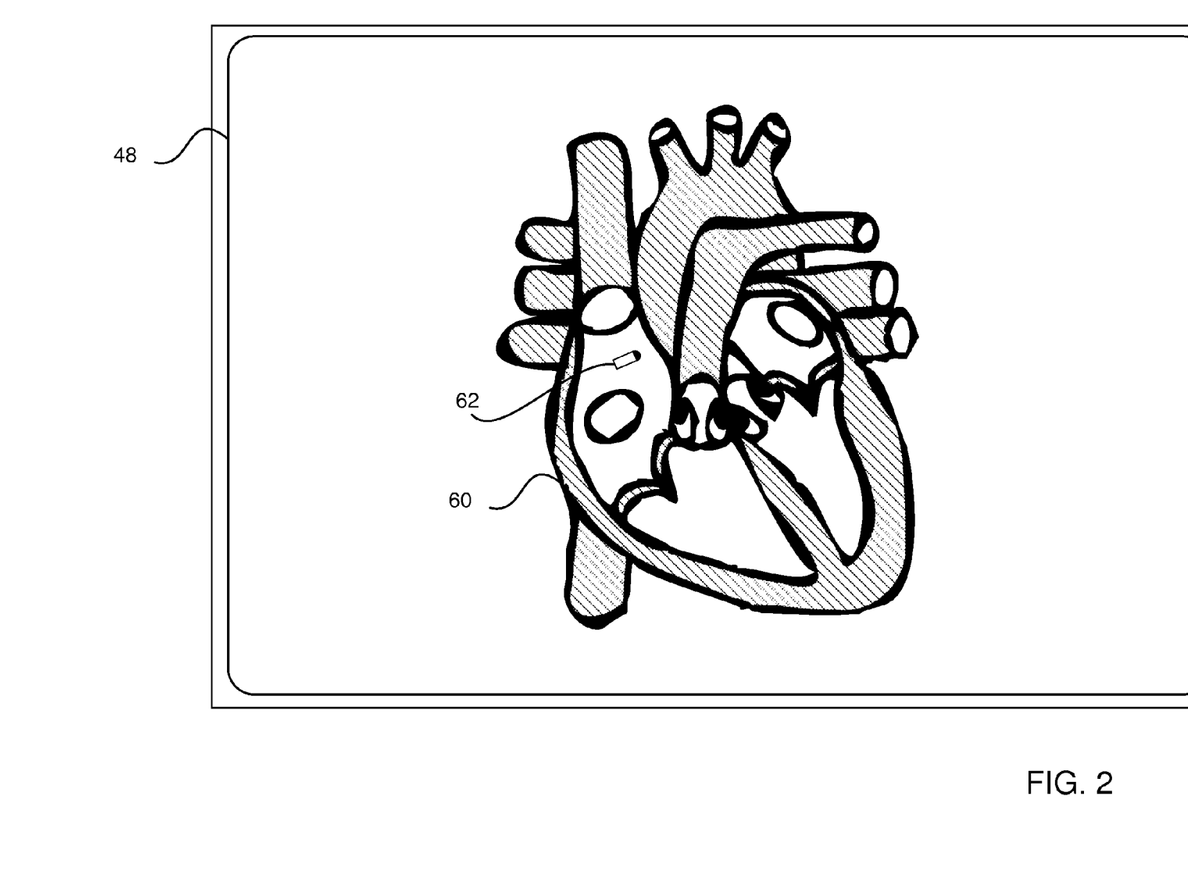
FIG. 2 is a schematic illustration of a display produced during mapping of a heart, according to an embodiment of the present invention.

FIG. 2 is a schematic illustration of display 48 produced during mapping of heart 34, according to an embodiment of the present invention. To map heart 34, an image 60 of the heart, herein assumed to be an image displaying three-dimensional (3D) characteristics of the heart, is presented to professional 28 on display 48. The image may be generated by any method known in the art, such as by using tracker module 30 to map 3D coordinates of surfaces of the chambers of the heart. The Carto® system or the Carto3® system may be used for such a 3D coordinate mapping. Alternatively or additionally, any other method, such as a magnetic resonance imaging (MRI) method, may be used to generate image 60.

Using image 60, the professional positions sensor 22 on different surfaces within the heart. The professional positions the sensor, (which is situated on distal end 32 of the probe) by manipulating a proximal end of the probe. The location of sensor 22 is tracked by module 30, and the location is presented to professional 28 as a cursor 62 overlaying image 60.

In some embodiments of the present invention, the generation of 3D image 60 described above, and the physiological mapping of heart 34 described below, are performed substantially simultaneously during one procedure. In the description herein, for clarity, the generation of the 3D image of the heart and the physiological mapping of the heart are assumed to be performed sequentially in two separate procedures. Those with ordinary skill in the art will be able to adapt the description, mutatis mutandis, for the case of a substantially simultaneous procedure.

Figure 3:
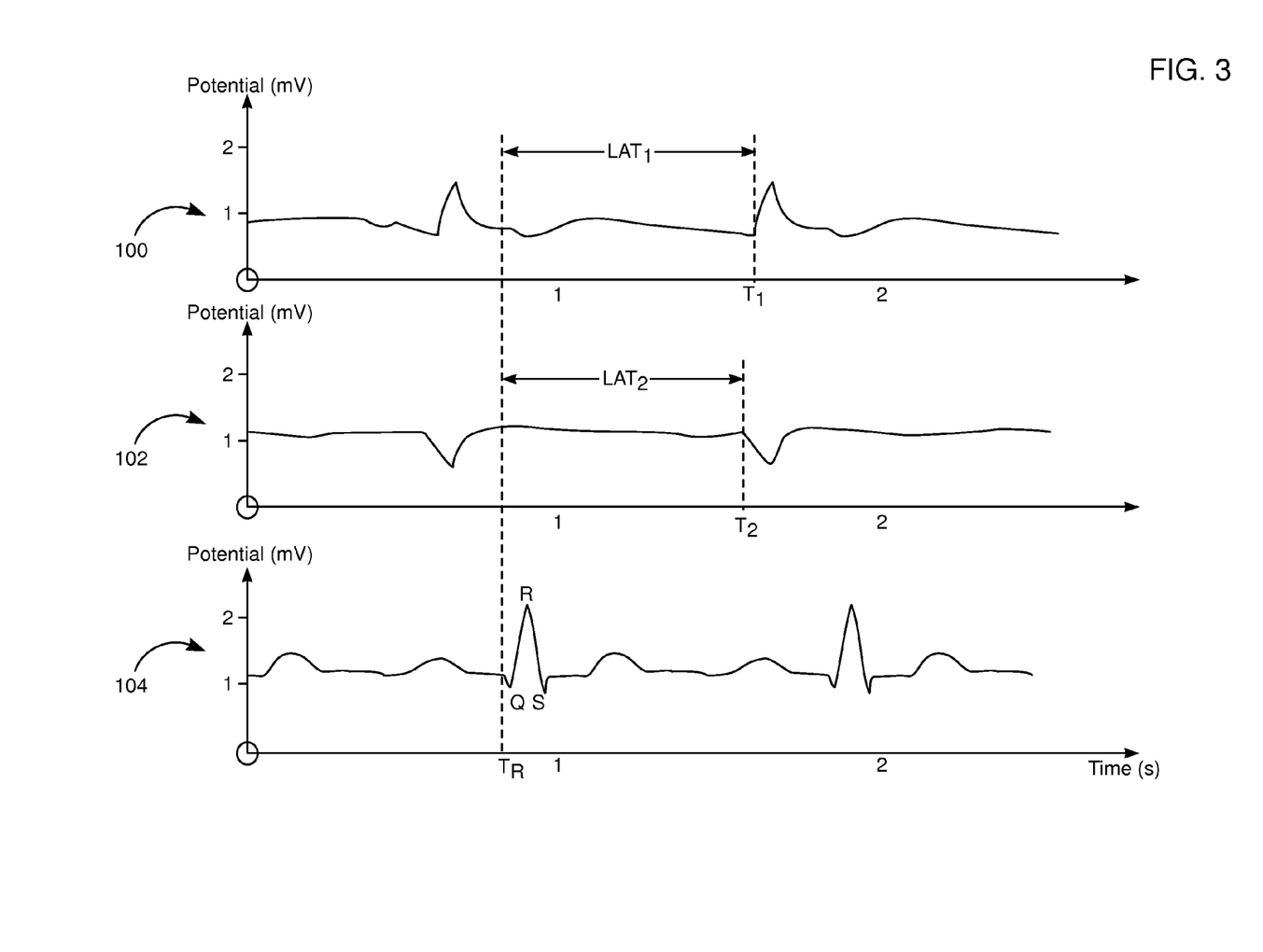
FIG. 3 shows schematic graphs of signals generated by the system of FIG. 1, according to an embodiment of the present invention.

FIG. 3 shows schematic graphs of signals generated by system 20, according to an embodiment of the present invention. For simplicity, in the following description except where otherwise stated, sensor 22 may be assumed to comprise an electrode. In addition, module 36 may be assumed to comprise an ECG module which is configured to sense electrical signals from the electrode, and processor 40 may be configured to analyze the sensed signals so as to generate as its physical parameter an LAT from the signal.

The graphs of FIG. 3 illustrate electrical activity occurring as heart 34 beats, and are also termed electrograms. In order to perform the mapping of system 20, which in this case comprises electrophysiological mapping, (as distinct from the 3D coordinate mapping described above), electrode 22 has to be in contact with a number of locations in heart 34. During each contact, processor 40 records the electrical activity, i.e., a set of pairs of potentials and times of occurrence of the potentials, of the location. Electrode 22 should be in contact with each location for a time period that allows sufficient data from the location to be recorded. Since the electrical activity of the heart is repetitive, a time period that is equal to, or greater than, the period for a complete heart beat may be sufficient. Thus, for a "typical" healthy heart beating at 70 beats per minute, a sufficient time period may typically be equal to or greater than about 850 ms. However, as explained below, the time period required may be less than, or greater than, the period of a heart beat.

An electrogram 100 is a schematic potential vs. time graph derived from a first signal on electrode 22, when it is in contact with a first location on a surface of heart 34. An electrogram 102 is a schematic potential vs. time graph derived from a second signal on the electrode, when it is in contact with a second location on the heart surface. A set of potential-time relationships for different locations on surfaces of heart 34, similar to those illustrated by electrograms 100 and 102, comprise the electrical activity of the heart, and such a set is recorded by processor 40.

An electrogram 104 is a schematic ECG potential vs. time graph of a signal on one of skin electrodes 29, illustrating the typical QRS complex of the signal. In order to fully characterize the set of potential-time relationships illustrated by electrograms 100 and 102, the potential-time relationships need to be referenced in time to each other. In embodiments of the present invention, the time referencing is accomplished by measuring to an instance in time, herein termed the reference instance, on a reference signal. Herein, by way of example, the reference signal is assumed to comprise the ECG potential vs. time signal. Also by way of example, the reference instance is assumed to be the beginning of the QRS complex, $T_R$, of the ECG signal. For any given location in the heart being mapped, the LAT of the electrical activity of the location may be defined in terms of the electrical activity satisfying a predefined condition. In the following description, the predefined condition is assumed to comprise a time of occurrence of the largest rapid deflection of the electrogram at the location, and the LAT is assumed to be the time from reference instance $T_R$ to the following onset of the largest rapid deflection of the electrogram of the location. LATs may be positive or negative. Methods for determining the time of occurrence of the largest rapid deflection of the electrogram, and other definitions and conditions for determining the LAT, will be familiar to those skilled in the art, and all such methods, definitions, and conditions are assumed to be comprised within the scope of the present invention.

In electrogram 100, the largest rapid deflection (after $T_R$) occurs at a time $T_1$, wherein the potential begins a rapid rise. The local activation time for the signal for the first location, i.e., a time period herein termed $LAT_1$, is the time from $T_R$ to $T_1$. In electrogram 102, the largest rapid deflection occurs at a time $T_2$, wherein the potential begins to fall rapidly. The local activation time for the signal for the second location, herein termed $LAT_2$, is the time from $T_R$ to $T_2$.

Figure 4:
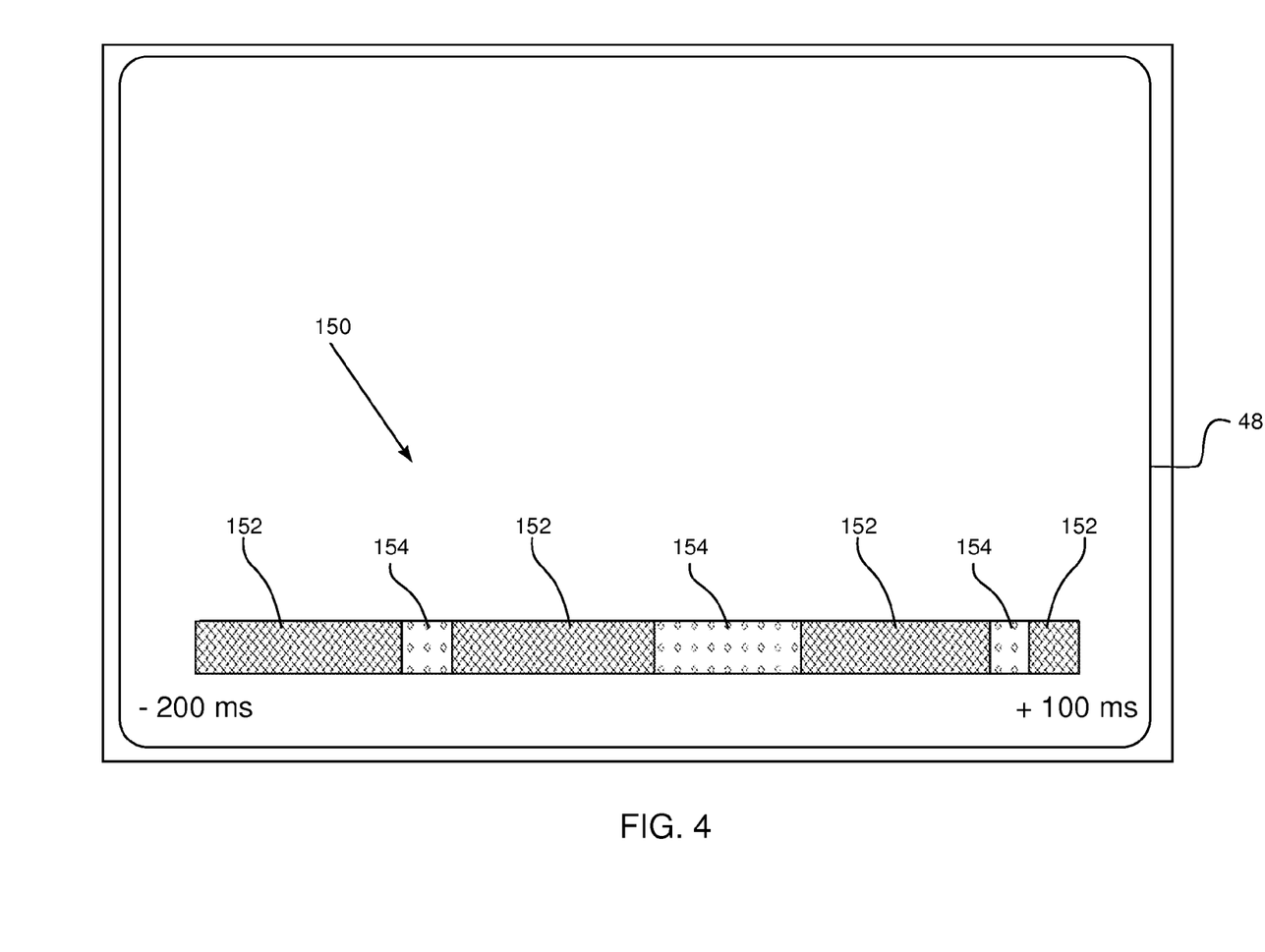
FIG. 4 is a schematic representation of local activation times (LATs), according to an embodiment of the present invention.

FIG. 4 is a schematic representation 150 of LATs, according to an embodiment of the present invention. Each location in a heart being mapped electrophysiogically has a characteristic LAT. Typically, an LAT is in the range from approximately −200 ms to approximately +100 ms, although other ranges are possible. In addition, the LATs for a particular heart form a continuum, so that within the range of possible LAT values there are typically no gaps. However, in an initial recording of electrical activity of a heart, some of the recorded time-varying potentials may not provide sufficient data to processor 40 for evaluation of an LAT, so that there is a sub-range of LATs wherein values of LATs have not been measured.

Representation 150 is a number line of the LATs. Since an LAT is measured in a unit of time, representation 150 is a time line. The time line illustrates a range of LATs comprising sets of times 152 wherein an LAT has been measured, and sets of times 154, wherein no evaluation has been made. Representation 150 is presented on display 48, and sets 152 and 154 are differentiated visually, typically by having different colors assigned to the two sets. Times 154, also termed herein missing times 154, comprise a sub-range of the complete range of LATs, wherein the LATs have not been evaluated.

Figure 5A:
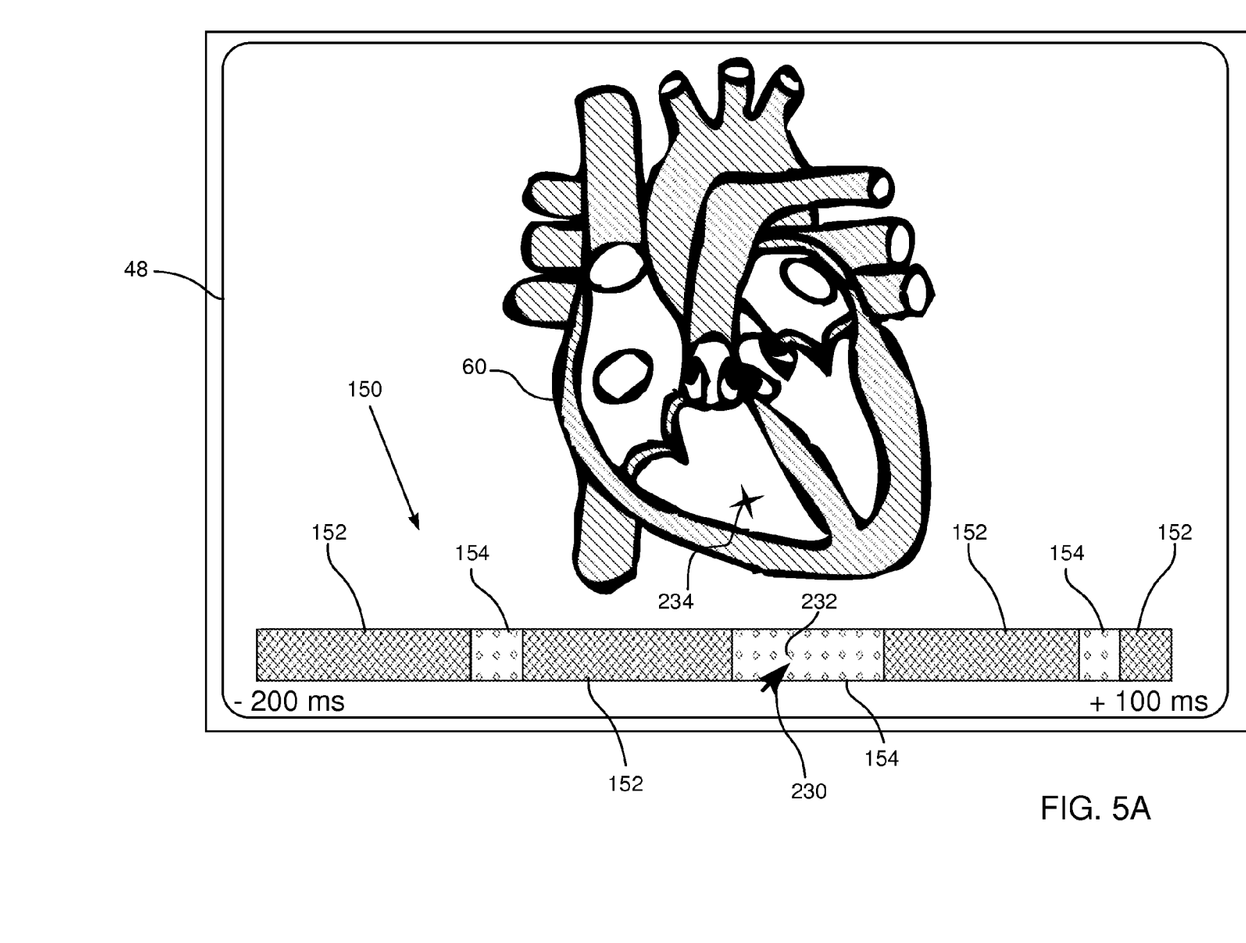
FIGS. 5A and 5B are schematic diagrams illustrating representations on a display, according to embodiments of the present invention.
Figure 5B:
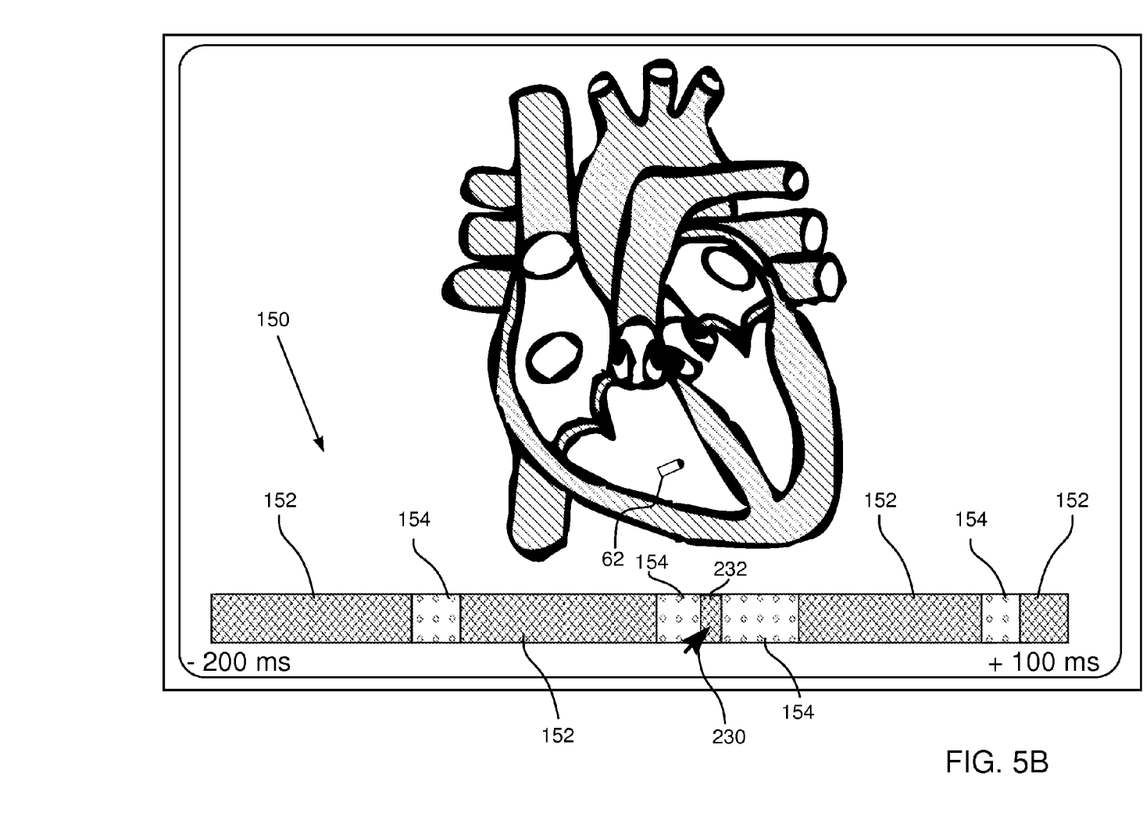
Figure 6:
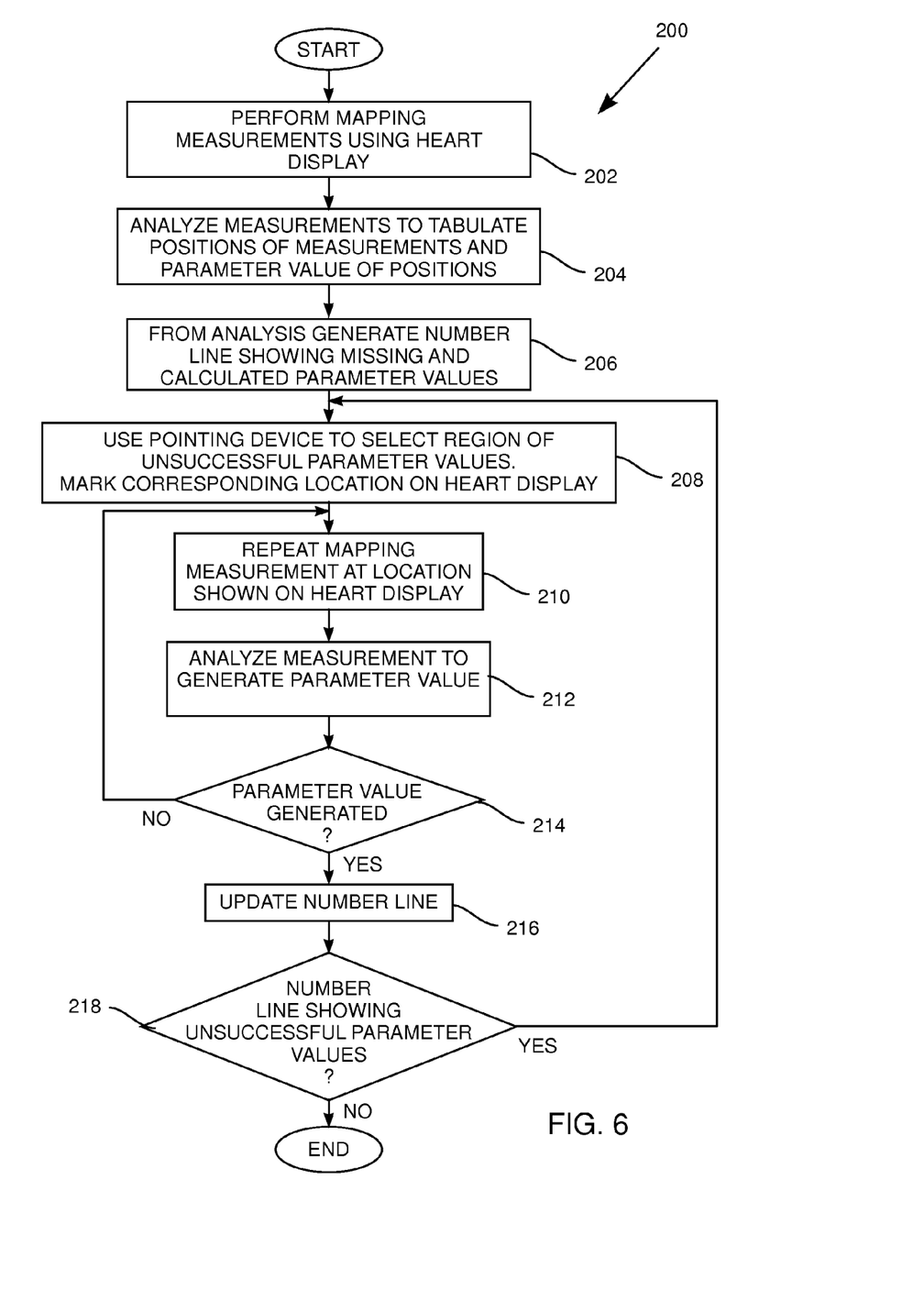
FIG. 6 is a flowchart of steps followed in the mapping system of FIG. 1, according to an embodiment of the present invention.

FIGS. 5A and 5B are schematic diagrams illustrating representations similar to representation 150 on display 48, according to embodiments of the present invention. FIG. 6 is a flowchart 200 of steps followed in mapping system 20, using the representations of FIGS. 5A and 5B, according to an embodiment of the present invention. For simplicity, FIGS. 5A and 5B assume that the physical parameter being mapped is an LAT, so that representations 150 are displayed as time lines.

In an initial step 202 of the flowchart, professional 28 performs an initial mapping of heart 34, by positioning sensor 22 on surfaces of the heart, substantially as described above for FIG. 2. Thus, professional 28 manipulates the distal end of probe 24, using cursor 62 on heart image 60, to position the distal end and its attached sensor 22 in contact with desired surfaces of the heart. In each location, processor 40 records the coordinates of the location, and also records the measurements for the physical parameter.

In the case of the parameter being an LAT, the measurements are time-varying potentials, which comprise a set of potential-time values. During the initial step, processor 40 also records a reference signal that is to be used to determine the reference instance for the LATs. As described above with respect to FIG. 3, the reference signal is assumed to be an ECG signal, and the reference instance is assumed to be the beginning of the QRS complex.

In an analysis step 204 processor 40, for each location, analyzes the respective set of measurements, to try to find a value of the physical parameter for the set.

For LATs, the measurements are potential-time values. In this case, for each set, the LAT may be measurable by the processor, or the LAT may not be measurable.

In a set that has a measurable LAT, the processor has been able to determine at least one reference time and at least one time for the following onset of the largest rapid deflection of the signal. Typically there is more than one pair of such times, in which case the processor may generate an average value of the LAT. Typically, although not necessarily, to achieve a measurable LAT for a given location, sensor 22, in this case an electrode, contacts the location, thereby sensing electrical signals generated at the location, for a time period corresponding to at least one complete beat.

The LAT may not be measurable for a number of reasons, such as electrode 22 not contacting a given location for a sufficient length of time, noise on the signal from the electrode, and/or noise on the reference signal.

For each set (having a measurable LAT or not having a measureable LAT) there is also a corresponding set of coordinates of the location at which the set has been recorded. The processor stores the results of the analysis as set 50 of pairs (FIG. 1). As shown in the example of set 50 illustrated in FIG. 1, for pairs 52 and 56, i.e., locations $(x_a, y_a, z_a)$ and $(x_c, y_c, z_c)$, the processor has measured respective values of the LAT; for pairs 54 and 58, i.e., locations $(x_b, y_b, z_b)$ and $(x_d, y_d, z_d)$, the processor has been unable to measure a value of the LAT.

In a line generation step 206, processor 40 displays the values of set 50 as number line 150 (FIG. 4). The number line illustrates values 152 of sets of physical parameters wherein the processor has been able to measure the parameter. The number line also illustrates sub-ranges 154 on the line, corresponding to sets of missing parameters, wherein the processor has been unable to measure a value of the physical parameter.

Thus, for LAT measurements, the displayed time line illustrates values of sets of times 152 wherein the processor has been able to measure an LAT. The displayed time line also illustrates sub-ranges on the time line, corresponding to sets of missing times 154, wherein the processor has been unable to measure an LAT. Each set of times 152 is continuous, and each set of regions corresponding to unmeasured or missing times 154 is also continuous.

In a selection step 208, processor 40 presents on display 48 image 60 of the heart, and number line 150. Operator 28 uses pointing device 39 to position a cursor 230 on a selected part 232 of one of missing parameters 154 (FIG. 5A). From set of pairs 50, processor 40 selects a pair corresponding to selected part 232, i.e., a pair where the processor was unable to measure a missing parameter. The selected pair has a known location, but an unknown parameter value, and processor marks the known location on image 60 with a marker 234, the marker indicating that the known location is a candidate for further measurement by the operator.

In a repeat step 210, the operator repositions distal end 32 to the location indicated by marker 234, typically by overlaying cursor 62 onto marker 234. Once the distal end is repositioned, processor 40 re-records the set of measurements for the physical parameter using sensor 22.

In a re-analysis step 212, processor 40 analyzes the re-recorded measurements, and in a first condition 214, the processor checks if a value of the physical parameter has been derived from the analysis.

If a parameter value has been derived, then in an update step 216, number line 150 is updated. Set 50 is also updated. Typically, while cursor 62 may remain, marker 234 is removed from image 60 since a parameter value has been found for the location indicated by the marker. FIG. 5B illustrates an updated time line for this case, with region 232 now being included in values 152.

If in condition 214, the processor has not been able to derive a parameter value from the re-recorded measurements, the flowchart returns to step 210, for the operator to repeat the measurement recording. Typically, a visual and/or an audio indication is provided to the operator that step 210 is being repeated.

A second condition 218 checks to see if there are any remaining missing values in sub-ranges 154. If there are missing values, the flowchart returns to step 208; if there are no missing values on number line 150, the flowchart finishes.

The above description has included mapping of LATs. However, it will be understood that the methods described may be adapted by those having ordinary skill in the art, without undue experimentation, for determining the values of other physical parameters of the heart or another organ of a subject. For example, in the case of the heart, other physical parameters may comprise the temperature or the contractility of the heart walls, respectively using a temperature sensor or a force sensor in place of sensor 22. Other organs that may be mapped include the bladder or the stomach.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
   measuring one or more physical parameters at multiple locations in an organ of a subject;
   analyzing the measured parameters to identify a range of the values, including at least one sub-range containing one or more measured parameters that did not identify a value;
   generating a number line comprising the identified range of the values and at least one of the one or more measured parameters that did not identify a value;
   receiving a selection from a user of a value from the at least one of the one or more measured parameters that did not identify a value; and
   responsive to the selection, displaying a candidate location for further measurement.

2. The method according to claim 1, wherein the organ comprises a heart.

3. The method according to claim 2, wherein the physical parameter is evaluated in response to one of a force exerted by the heart and a temperature of the heart.

4. The method according to claim 2, wherein the physical parameter is evaluated in response to electrical activity of the heart.

5. The method according to claim 4, wherein the physical parameter comprises respective local activation times (LATs) of the multiple locations in the heart.

6. The method according to claim 5, wherein measuring the values comprises recording respective time-varying electrical potentials at the multiple locations, and wherein analyzing the measured values comprises determining the respective LATs in response to applying a predefined condition to the recorded time-varying electrical potentials.

7. The method according to claim 2, wherein displaying the candidate location comprises displaying an image of the heart to the user, and indicating on the image the candidate location.

8. The method according to claim 1, wherein generating the number line comprises displaying to the user a first visual representation of values that were measured, and a second visual representation, different from the first visual representation, of the at least one sub-range.

9. The method according to claim 8, wherein receiving the selection from the user comprises the user operating a pointing device to select a region in the second visual representation.

10. Apparatus, comprising:
    a probe, which is configured to provide signals used to measure one or more physical parameters at multiple locations in an organ of a subject; and
    a processor which is configured to:
    analyze the measured parameters to identify a range of values, including at least one sub-range containing one or more measured parameters that did not identify a value;
    generate a number line comprising the identified range of the values and at least one of the one or more measured parameters that did not identify a value;

receive a selection from a user of a value from the at least one of the one or more measured parameters that did not identify a value; and responsive to the selection, display a candidate location for further measurement.

11. The apparatus according to claim 10, wherein the organ comprises a heart.

12. The apparatus according to claim 11, wherein the physical parameter is evaluated in response to one of a force exerted by the heart and a temperature of the heart.

13. The apparatus according to claim 11, wherein the physical parameter is evaluated in response to electrical activity of the heart.

14. The apparatus according to claim 13, wherein the physical parameter comprises respective local activation times (LATs) of the multiple locations in the heart.

15. The apparatus according to claim 14, wherein the signals comprise time-varying electrical potentials, and wherein measuring the values comprises recording respective signals at the multiple locations, and wherein analyzing the measured values comprises determining the respective LATs in response to applying a predefined condition to the recorded signals.

16. The apparatus according to claim 11, wherein displaying the candidate location comprises displaying an image of the heart to the user, and indicating on the image the candidate location.

17. The apparatus according to claim 10, wherein generating the number line comprises displaying to the user a first visual representation of values that were measured, and a second visual representation, different from the first visual representation, of the at least one sub-range.

18. The apparatus according to claim 17, wherein receiving the selection from the user comprises the user operating a pointing device to select a region in the second visual representation.

* * * * *